(12) United States Patent
Denker et al.

(10) Patent No.: US 7,720,547 B2
(45) Date of Patent: May 18, 2010

(54) EXTRACORPOREAL POWER SUPPLY WITH A WIRELESS FEEDBACK SYSTEM FOR AN IMPLANTED MEDICAL DEVICE

(75) Inventors: Stephen Denker, Mequon, WI (US); Cherik Bulkes, Sussex, WI (US); Arthur J. Beutler, Greendale, WI (US)

(73) Assignee: Kenergy, Inc., Mequon, WI (US)

( * ) Notice: Subject to any disclaimer, the term of this patent is extended or adjusted under 35 U.S.C. 154(b) by 963 days.

(21) Appl. No.: 11/325,130

(22) Filed: Jan. 4, 2006

(65) Prior Publication Data

US 2007/0156204 A1    Jul. 5, 2007

(51) Int. Cl.
*A61N 1/378* (2006.01)
(52) U.S. Cl. .......................... 607/61; 607/33
(58) Field of Classification Search ............. 607/32, 607/60, 61, 33
See application file for complete search history.

(56) References Cited

U.S. PATENT DOCUMENTS

| | | | |
|---|---|---|---|
| 5,411,535 A | 5/1995 | Fujii et al. | |
| 5,531,774 A | 7/1996 | Schulman et al. | |
| 5,713,939 A | 2/1998 | Nedungadi et al. | |
| 5,876,425 A | 3/1999 | Gord et al. | |
| 6,445,953 B1 | 9/2002 | Bulkes et al. | |
| 6,772,011 B2 * | 8/2004 | Dolgin | 607/60 |
| 2003/0014090 A1 * | 1/2003 | Abrahamson | 607/60 |
| 2003/0135246 A1 * | 7/2003 | Mass et al. | 607/60 |
| 2005/0096702 A1 | 5/2005 | Denker et al. | |
| 2005/0107847 A1 | 5/2005 | Gruber et al. | |
| 2005/0187584 A1 | 8/2005 | Denker et al. | |
| 2005/0288739 A1 * | 12/2005 | Hassler et al. | 607/61 |
| 2006/0161225 A1 * | 7/2006 | Sormann et al. | 607/61 |

FOREIGN PATENT DOCUMENTS

| | | |
|---|---|---|
| WO | WO 99/44684 | 9/1999 |
| WO | WO 01/56653 | 8/2001 |
| WO | WO 2004/018037 | 3/2004 |

* cited by examiner

*Primary Examiner*—George R Evanisko
*Assistant Examiner*—Joseph M Dietrich
(74) *Attorney, Agent, or Firm*—Quarles & Brady LLP; George E. Haas

(57) ABSTRACT

A medical device adapted for implantation into a patient receives electrical power from an extracorporeal power supply. The medical device has a first receiver for a first wireless signal, a power circuit that extracts energy from the first wireless signal to power the medical device, and a feedback signal generator that transmits a second wireless signal indicating a magnitude of energy extracted from the first wireless signal. The extracorporeal power supply includes a source of electrical power and a power transmitter that emits the first wireless signal. A second receiver enables the extracorporeal power supply to receive the second wireless signal. A feedback controller manipulates the first wireless signal in response to the second wireless signal to ensure that sufficient electrical energy is provided to the medical device without wasting electrical power from the source.

29 Claims, 2 Drawing Sheets

US 7,720,547 B2

EXTRACORPOREAL POWER SUPPLY WITH A WIRELESS FEEDBACK SYSTEM FOR AN IMPLANTED MEDICAL DEVICE

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The present invention relates to medical devices that are implanted into the body of an animal, and more particularly to control of electrical power supplied to the implanted medical device from an extracorporeal power supply.

2. Description of the Related Art

A remedy for people with slowed or disrupted natural heart activity is to implant a cardiac pacing device which is a small electronic apparatus that stimulates the heart to beat at regular rates.

Typically a battery powered pacing device is implanted in the patient's chest and has sensor electrodes that detect electrical impulses associated with in the heart contractions. These sensed impulses are analyzed to determine when abnormal cardiac activity occurs, in which event a pulse generator is triggered to produce electrical pulses. Wires carry these pulses to electrodes placed adjacent specific cardiac muscles, which when electrically stimulated contract the heart chambers. It is important that the electrodes be properly located to produce contraction of the heart chambers.

Modern cardiac pacing devices vary the stimulation to adapt the heart rate to the patient's level of activity, thereby mimicking the heart's natural activity. The pulse generator modifies that rate by tracking the activity of the sinus node of the heart or by responding to other sensor signals that indicate body motion or respiration rate.

U.S. Patent Application Publication No. 2005-0096702 describes a cardiac pacemaker that has an implanted pacing device implanted in a vein or artery of the patient's heart. The pacing device responds to detecting abnormal electrical cardiac activity by applying a voltage pulse across a pair of electrodes, thereby stimulating muscles adjacent the vein or artery which causes contraction of the heart. The implanted pacing device is powered by energy derived from a radio frequency signal received from an extracorporeal power supply. The derived energy charges a capacitor or other storage mechanism in the pacing device which provides electrical voltage for the simulation.

Heretofore, an open loop system was employed to supply power to the implanted device from the extracorporeal power supply. That system was designed to meet the worst case power demand so that the implanted device had sufficient power to function in every situation. However, this resulted in the excessive energy being furnished to the implanted device the vast majority of the time when less power was needed. The open loop system was an inefficient use of the battery power in the extracorporeal power supply.

It is desirable to control the transmission of the radio frequency signal to the implanted medical device in a manner that ensures that its energy storage device always is sufficiently charged without providing excessive energy.

SUMMARY OF THE INVENTION

A medical apparatus comprises an extracorporeal power supply and a medical device adapted for implantation into a patient. The medical device comprises a first receiver for a first wireless signal, a power circuit that extracts energy from the first wireless signal to power the medical device, and a feedback signal generator that transmits a second wireless signal indicating a magnitude of energy extracted from the first wireless signal.

The extracorporeal power supply includes a source of electrical power, a power transmitter that emits the first wireless signal, a second receiver for the second wireless signal. A feedback controller is connected to the second receiver and the power transmitter and controls transmission of the first wireless signal in response to the second wireless signal. The control of the first wireless signal ensures that sufficient electrical energy is provided to the medical device without wasting electrical power from the source.

In a preferred embodiment, the duty cycle of the first wireless signal is varied to control the amount of energy delivered to the medical device. The medical device produces an electrical voltage from the received first wireless signal. The frequency of the second wireless signal is defined in response to the magnitude of the electrical voltage and thereby indicates the amount of energy extracted from the first wireless signal for powering the medical device.

Another aspect of the present invention provides a mechanism by which operational data and commands are sent to the medical device via the first wireless signal.

A further aspect of the present invention enables the medical device to send operational parameters or other data to a receiver outside the patient. An alarm apparatus alerts personnel when such operational parameters or other data indicate and abnormality.

DETAILED DESCRIPTION OF THE INVENTION

Although the present invention is being described in the context of components for a cardiac pacing system, it can be used to control supplying energy from an extracorporeal power supply to other types of implanted medical devices.

Figure 1:
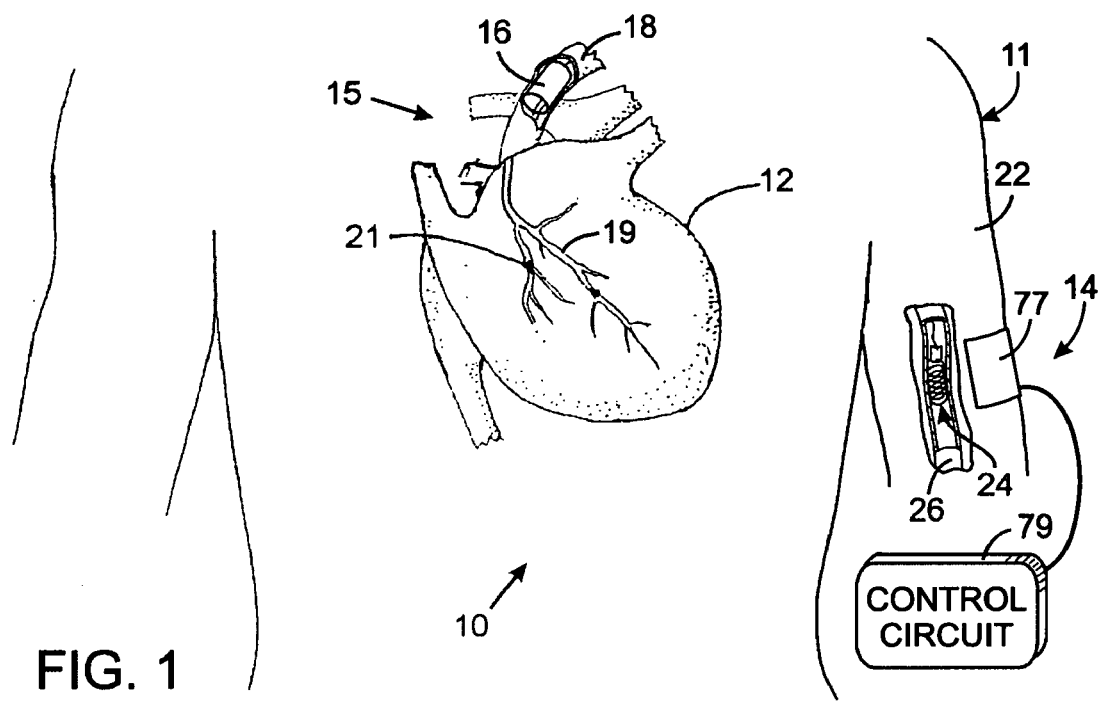
FIG. 1 depicts a cardiac pacing system attached to a medical patient.

Initially referring to FIG. 1, a medical apparatus, in the form of a cardiac pacing system 10 for electrically stimulating a heart 12 to contract, comprises an extracorporeal power supply 14 and a medical device 15 implanted in the circulatory system of a human patient 11. The medical device 15 receives a radio frequency (RF) signal from the power supply 14 worn outside the patient and the implanted electrical circuitry is electrically powered by the energy of that signal. At appropriate times, the medical device 15 delivers an electrical stimulation pulse into the surrounding tissue of the patient thereby producing a contraction of the heart 12.

Figure 2:
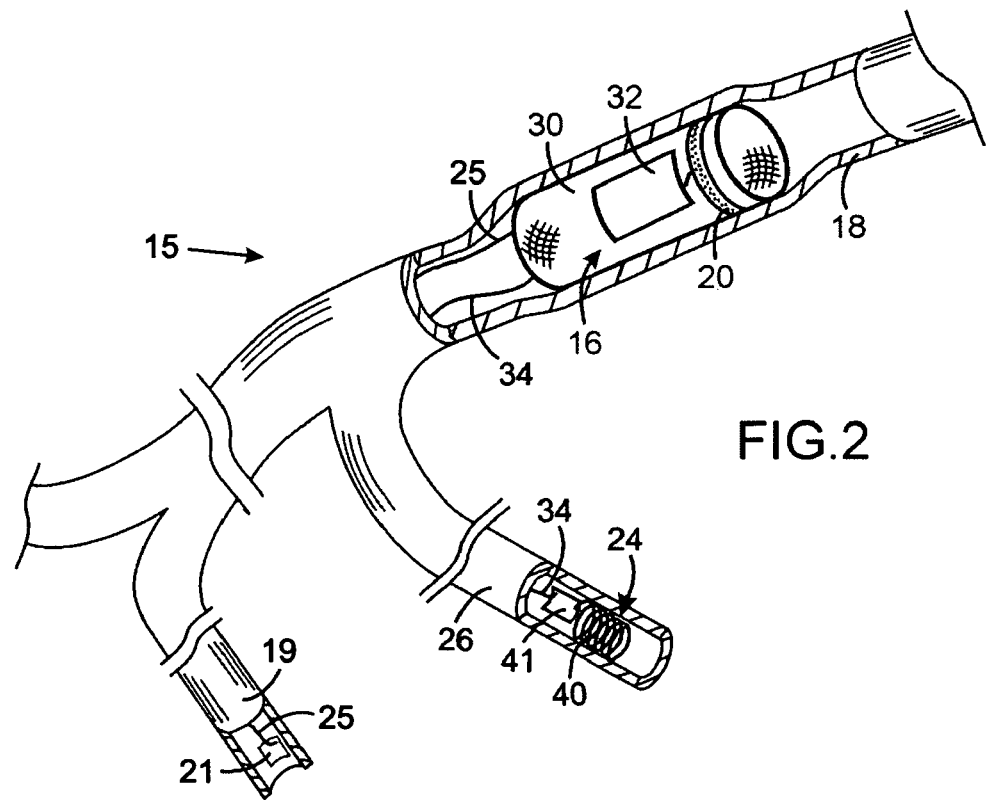
FIG. 2 is an isometric, cut-away view of a patient's blood vessels in which a receiver antenna, a stimulator and an electrode of an intravascular medical device have been implanted at different locations.

Referring to FIGS. 1 and 2, the exemplary implanted medical device 15 includes an intravascular stimulator 16 located in a vein or artery 18 in close proximity to the heart 12. One or more electrical wires 25 lead from the stimulator 16 through the cardiac vasculature to one or more locations in smaller blood vessels 19 at which stimulation of the heart is desired. At such locations, the electrical wire 25 is connected to a remote electrode 21 secured to the blood vessel wall.

Because the stimulator 16 of the medical device 15 is near the heart and relatively deep in the chest of the human medical patient, an assembly 24 of transmit and receive antennas for radio frequency signals are implanted in a vein or artery 26 of the patient's upper right arm 22 at a location in close proximity to the extracorporeal power supply 14. That arm vein or artery 26 is significantly closer to the skin and thus antenna assembly 24 picks up a greater amount of the energy of the radio frequency signal emitted by the power supply 14, than if the antenna assembly was located on the stimulator 16. Alternatively, another limb, neck or other area of the body with an adequately sized blood vessel close to the skin surface of the patient can be used. The antenna assembly 24 is connected to the stimulator 16 by a cable 34.

As illustrated in FIG. 2, the intravascular stimulator 16 has a body 30 constructed similar to well-known expandable vascular stents. The stimulator body 30 comprises a plurality of wires formed to have a memory defining a tubular shape or envelope. Those wires may be heat-treated platinum, Nitinol, a Nitinol alloy wire, stainless steel, plastic wires or other materials. Plastic or substantially nonmetallic wires may be loaded with a radiopaque substance which provides visibility with conventional fluoroscopy. The stimulator body 30 has a memory so that it normally assumes an expanded configuration when unconfined, but is capable of assuming a collapsed configuration when disposed and confined within a catheter assembly, as will be described. In that collapsed state, the tubular body 30 has a relatively small diameter enabling it to pass freely through the vasculature of a patient. After being properly positioned in the desired blood vessel, the body 30 is released from the catheter and expands to engage the blood vessel wall. The stimulator body 30 and other components of the medical device 15 are implanted in the patient's circulatory system a catheter.

The body 30 has a stimulation circuit 32 mounted thereon and, depending upon its proximity to the heart 12, may hold a first electrode 20 in the form of a ring that encircles the body. Alternatively, when the stimulator 16 is relatively far from the heart 12, the first electrode 20 can be remotely located in a small cardiac blood vessel, much the same as a second electrode 21. The second electrode 21 and the first electrode when located remotely from the stimulator 16 can be mounted on a collapsible body of the same type as the stimulator body 30.

Figure 3:
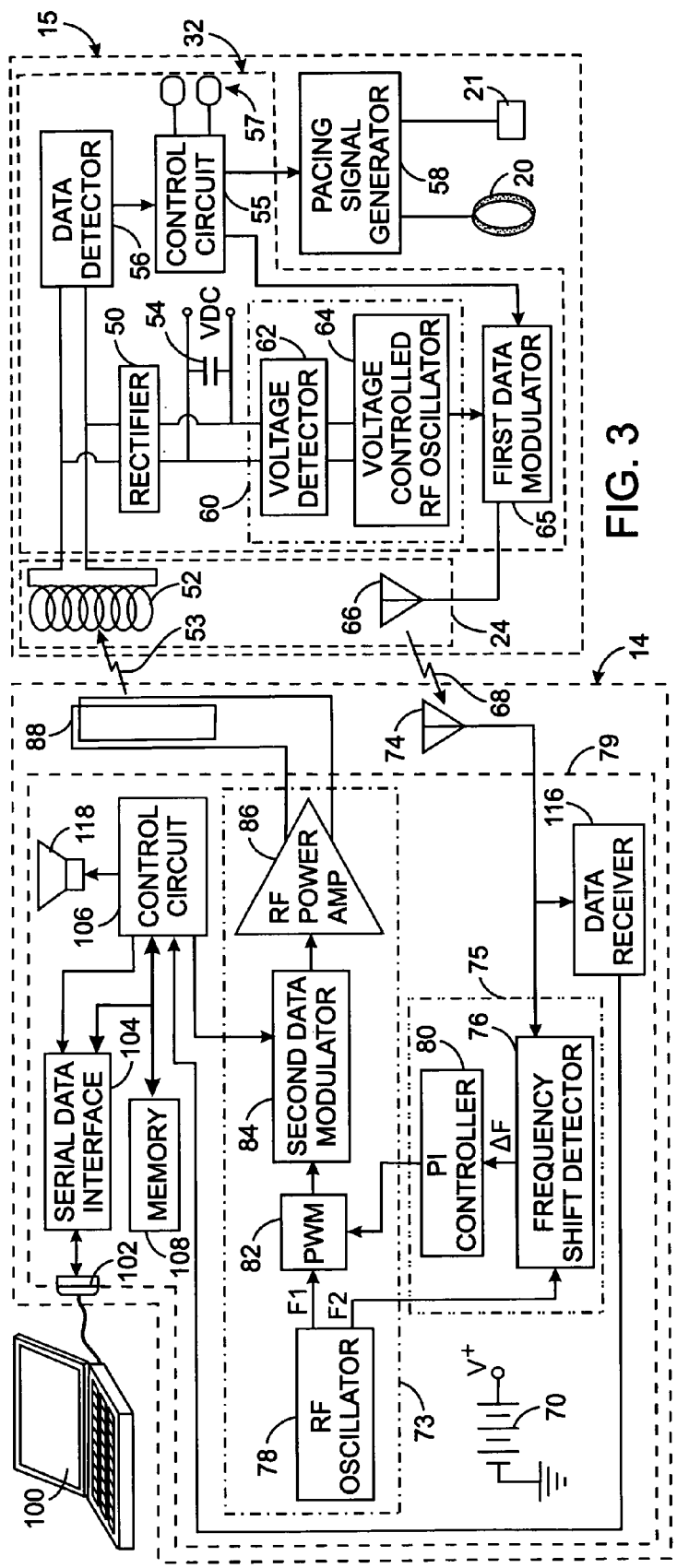
FIG. 3 is a block schematic diagram of the electrical circuitry for the cardiac pacing system.

With reference to FIG. 3, the stimulation circuit 32 includes a first receive antenna 52 within the antenna assembly 24 and that antenna is tuned to pick-up a first wireless signal 53 at a first radio frequency F1. The first receive antenna 52 is coupled to a data detector 56 that recovers data and commands carried by the first wireless signal 53. That data specifies operational parameters of the medical device 15, such as the duration that a stimulation pulse is applied to the electrodes 20 and 21. The recovered data is sent to a control circuit 55 for that medical device, which stores the operational parameters for use in controlling operation of a pacing signal generator 58 that applies tissue stimulating voltages pulses across the electrodes 20 and 21.

The control circuit 55 also is connected to pair of sensor electrodes 57 that detect electrical activity of the heart and provide conventional electrocardiogram signals which are utilized to determine when cardiac pacing should occur. Additional sensors for other physiological characteristics, such as temperature, blood pressure or blood flow, may be provided and connected to the control circuit 55. The control circuit stores a histogram of pacing, data related to usage of the medical device, and other information which can be communicated to the extracorporeal power supply 14 or another form of a data gathering device that is external to the patient 11, as will be described.

The first receive antenna 52 also is connected to a rectifier 50 that extracts energy from the received first wireless signal. That energy is used to charge a storage capacitor 54 that supplies electrical power to the components of the implanted medical device 15. Specifically, the radio frequency, first wireless signal 53 is rectified to produce a DC voltage (VDC) that is applied across the storage capacitor 54.

The DC voltage produced by the rectifier 50 also is applied to a feedback signal generator 60 comprising a voltage detector 62 and a voltage controlled, first radio frequency oscillator 64. The voltage detector 62 senses and compares the DC voltage to a nominal voltage level desired for powering the medical device 15. The result of that comparison is a control voltage that indicates the relationship of the actual DC voltage derived from the received first wireless signal 53 and the nominal voltage level. The control voltage is fed to the control input of the voltage controlled, first radio frequency oscillator 64 which produces an output signal at a radio frequency that varies as a function of the control voltage. For example, the first radio frequency oscillator 64 has a center, or second frequency F2 from which the actual output frequency varies in proportion to the polarity and magnitude of the control signal and thus deviation of the actual DC voltage from the nominal voltage. For example, the first radio frequency oscillator 64 has a first frequency of 100 MHz. and varies 100 kHz per volt of the control voltage with the polarity of the control voltage determining whether the oscillator frequency decreases or increases from the second frequency F2. For this exemplary oscillator, if the nominal voltage level is five volts and the output of the rectifier 50 is four volts, or one volt less than nominal, the output of the voltage controlled, first radio frequency oscillator 64 is 99.900 MHz. (100 MHz-100 kHz). That output is applied to a first transmit antenna 66 of the implanted medical device 15, which thereby emits a second wireless signal 68.

As noted previously, the electrical energy for powering the medical device 15 is derived from the first wireless signal sent by the extracorporeal power supply 14. As will be described in greater detail hereinafter, the extracorporeal power supply 14 periodically transmits pulses of the first wireless signal 53. The first wireless signal 53 is pulse width modulated to vary the magnitude of energy received by the implanted medical device 15. The pulse width modulation is manipulated to control the amount of energy the medical device receives to ensure that it is sufficiently powered without wasting energy from the battery 70 in the extracorporeal power supply 14. Alternatively, the first wireless signal 53 can be modulated by amplitude modulation to vary the magnitude of energy received by the implanted medical device 15.

To control the energy of the first wireless signal 53, the extracorporeal power supply 14 contains a second receive antenna 74 that picks up the second wireless signal 68 from the implanted medical device 15. Because the second wireless signal 68 indicates the level of energy received by medical device 15, this enables extracorporeal power supply 14 to determine whether medical device should receive more or less energy. The second wireless signal 68 is sent from the second receive antenna 74 to a feedback controller 75 which comprises a frequency shift detector 76 and a proportional-integral (PI) controller 80. The second wireless signal 68 is applied to the frequency shift detector 76 which also receives a reference signal at the second frequency F2 from a second radio frequency oscillator 78. The frequency shift detector 76 compares the frequency of the received second wireless signal 68 to the second frequency F2 and produces a deviation signal ΔF indicating a direction and an amount, if any, that the frequency of the second wireless signal has been shifted from the second frequency F2. As described previously, the voltage controlled, first radio frequency oscillator 64, in the medical device 15, shifts the frequency of the second wireless signal 68 by an amount that indicates the voltage from rectifier 50 and thus the level of energy derived from the first wireless signal 53 for powering the implanted medical device 15.

The deviation signal ΔF is applied to the input of the proportional-integral (PI) controller 80 which applies a transfer function given by the expression $GAIN/(1+s_i \cdot \tau)$, where the GAIN is a time independent constant gain factor of the feedback loop, τ is a time coefficient in the LaPlace domain and $s_i$ is the LaPlace term containing the external frequency applied to the system The output of the proportional integral controller 80 is an error signal indicating an amount that the voltage (VDC) derived by the implanted medical device 15 from the first wireless signal 53 deviates from the nominal voltage level. That error signal corresponds to an arithmetic difference between a setpoint frequency and the product of a time independent constant gain factor, and the time integral of the deviation signal.

Figure 4:
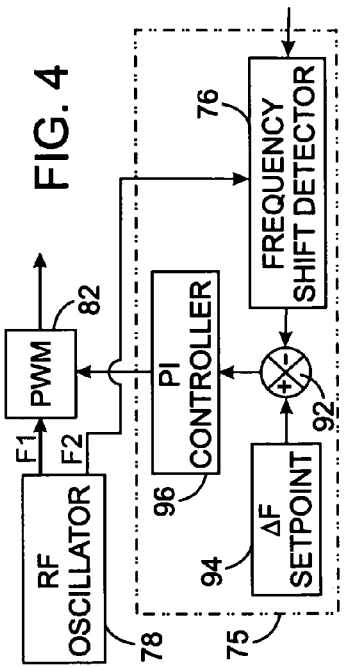
FIG. 4 is a schematic diagram showing a modified version of a portion of the electrical circuitry for the cardiac pacing system.

FIG. 4 illustrates an alternative embodiment of a feedback controller 75 for the extracorporeal power supply 14. As previously described, the implanted medical device 15 emits the second wireless signal 68 that increases and decreases in frequency to indicate whether the DC voltage produced by the rectifier 50 is above and below a nominal voltage level desired for powering the device. Alternatively, the frequency of the second wireless signal 68 may vary unidirectionally to indicate the magnitude of the DC voltage produced by the rectifier 50. For example, the second frequency F2 may increase by an amount indicative of the DC voltage. Assume that the second frequency F2 is 100 MHz, the nominal voltage level is five volts and that the frequency of the second wireless signal 68 varies 100 kHz per volt. Then, when the rectifier 50 is producing the desired five volts, the frequency of the second wireless signal 68 will be 100.5 MHz (100 MHz+500 kHz). When the load on the rectifier 50 causes the voltage to decrease to 4.9 volts, the frequency shifts to 100.490 MHz. If the setpoint frequency was 100.500 MHz, the difference is now −10 kHz and will be used to generate a corrective input causing the transmitter to increase it's output such that the rectifier voltage will return to 5.0 volts. With this alternative, when the extracorporeal power supply 14 receives the second wireless signal 68, the frequency shift detector 76 produces a deviation signal ΔF indicating the difference between the actual frequency of that wireless signal and the second frequency F2. That deviation signal is applied to an inverting input of a summation circuit 92 which also receives a fixed value ΔF setpoint 94 that corresponds to the value of the deviation signal when the rectifier 50 in the implanted medical device 15 is producing the nominal DC voltage (e.g. 5 volts). The summation circuit 92 produces an output signal indicating the polarity and magnitude that the rectifier's output voltage deviates from that nominal voltage level. That output signal is applied to the input of a proportional integral controller 96 that produces a error signal which is the same as that produced by the embodiment in FIG. 3.

Regardless of type of feedback controller 75 that is employed, the error signal is sent to the control input of a pulse width modulator (PWM) 82 which forms an amplitude modulator within a power transmitter 73 and produces at output signal that is on-off modulated as directed by the error input. For example, a 100% output implies that the signal is on 100% of the time, and off 0% of the time. As another example, when a 25% output is desired, the output signal will be on for 25% of the time, and off for 75% of the time. The rate at which this cycle repeats is a function on the amount of permissible output ripple. For example, a signal having a 10 kHz frequency, or 100 μs cycle period, would be adequate for a base transmit frequency of 10 MHz. In this case, within one 100 μs cycle and 25% duty cycle, the on-time would be 25 μs containing 250 cycles of the 10 MHz output frequency. The output from the pulse width modulator (PWM) 82 is fed to a second data modulator 84 which modulates the signal with data for the medical device 15, as will be described.

The resultant signal is amplified by a radio frequency power amplifier 86 having an output to which a transmit antenna 88 is connected. The transmit antenna 88 may be of the type described in U.S. Pat. No. 6,917,833. The antennas 74 and 88 in the extracorporeal power supply 14 are contained within a patch 77, shown in FIG. 1, which is adhesively applied to the skin of the patient's upper arm 22. The antennas in the patch 77 are connected to a module 79 that contains the remainder of the electronic circuitry for the extracorporeal power supply.

The transmit antenna 88 emits the first wireless signal 53 that, as described previously, is received by antenna 52 within the implanted medical device 15. The duty cycle of this first wireless signal 53 varies so as to provide different amounts of the electrical energy, thereby ensuring that the implanted medical device is always properly powered. In other words, as the DC voltage produced by the rectifier 50 within the implanted medical device 15 varies from the desired operating voltage, the feedback circuit comprising feedback signal generator 60 and feedback controller 75, cause a change in the duty cycle of the first wireless signal 53 to either increase or decrease the energy of that signal such that the DC voltage in the implanted medical device is maintained at a constant level. This level is preset in the external device.

In addition to transmitting electrical energy to the implanted medical device 15, the extracorporeal power supply 14 transmits operational parameters which configure the functionality of the medical device. The implanted medical device 15 also sends operational data to the extracorporeal power supply. A data input device, such as a personal computer 100, enables a physician or other medical personnel to specify operating parameters for the implanted medical device 15. Such operating parameters may define the duration of each stimulation pulse, an interval between atrial and ventricular pacing, and thresholds for initiating pacing. The data defining those operating parameters are transferred to the extracorporeal power supply 14 via a connector 102 connected to the input of a serial data interface 104. The data received by the serial data interface 104 can be applied to a microprocessor based control circuit 106 or stored directly in a memory 108.

Figure 5:
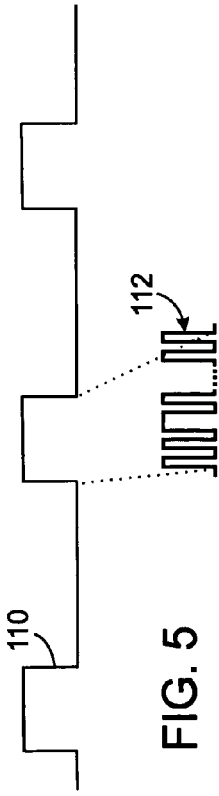
FIG. 5 illustrates the waveform of a radio frequency signal by which energy and data are transmitted to the intravascular medical device.

When new configuration parameters are received, the control circuit 106 initiates a transfer of those parameters from the memory 108 to the data input of the second data modulator 84. The transfer is accomplished by sending the parameters to the second data modulator 84 which also receives the output signal from the pulse width modulator 82. That output signal has a square waveform 110 depicted in FIG. 5 in which the duty cycle varies depending upon the desired magnitude of the electrical energy to be sent to the implanted medical device 15. The second data modulator 84 transforms each pulse of the square waveform 110 into a series of sub-pulses 112 thereby encoding the waveform with the parameter data. The resultant composite signal is then transmitted via the RF power amplifier 86 and the transmit antenna 88 to the implanted medical device 15 as the first wireless signal 53.

The data detector 56 within the implanted medical device 15 extracts the sub-pulses 112 from the first wireless signal 53 and decodes the extracted operating parameters which then are sent to the control circuit 55. The control circuit stores the operating parameters for use in controlling the medical device.

Furthermore, the control circuit may include sensors for physiological characteristics of the patient 11, such as heart rate or pressure within the blood vessel in which the medical device 15 is implanted. The sensed data is transmitted from the implanted medical device 15 to the extracorporeal power supply 14 via the second wireless signal 68. Specifically, the control circuit 55 sends the physiological data to the first data modulator 65 which modulates the signal produced by the voltage controlled, first radio frequency oscillator 64 with that data.

Data specifying operational conditions of the implanted medical device 15 also can be transmitted via the second wireless signal 68. For example, if the implanted medical device 15 fails to receive the first wireless signal 53 for a predefined period of time. The control circuit 55 generates alarm data which it transmitted via the second wireless signal 68 to alert a data receiver outside the patient of a malfunction of the cardiac pacing system 10. When the extracorporeal power supply 14 receives the second wireless signal 68, the data receiver 116 extracts data which then is transferred to the control circuit 106. Upon interpreting the data as indicating an alarm condition, control circuit 106 activates an alarm, such as by producing an audio signal via a speaker 118 or activate light emitters to produce a visual indication of the alarm. An alarm indication also can be sent via the serial data interface 104 to an external device, such as personal computer 100. In other situations, a wireless communication apparatus, such as a cellular telephone, may be integrated into the extracorporeal power supply 14 to transmit an alarm signal to a central monitoring facility.

The foregoing description was primarily directed to preferred embodiments of the invention. Even though some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

The invention claimed is:

1. A medical apparatus comprising an extracorporeal power supply forming a wireless closed loop system with a medical device adapted for implantation into a patient, wherein:

the medical device comprises a first receiver for a first wireless signal, a power circuit that extracts energy from the first wireless signal to power the medical device, and a feedback signal generator that transmits a second wireless signal having a frequency that varies to indicate an amount of energy extracted from the first wireless signal; and the extracorporeal power supply comprises a source of electrical power, a power transmitter that emits the first wireless signal, a second receiver for the second wireless signal, a feedback controller connected to the second receiver and the power transmitter to control transmission of the first wireless signal in response to frequency variation of the second wireless signal, the extracorporeal power supply further comprises a source of data specifying an operational parameter for the medical device and a data modulator coupled to the source of data and the power transmitter to modulate the first wireless signal in response to the data, wherein the first wireless signal comprises power pulses which vary in width in response to the second wireless signal, and each power pulse comprises a series of sub-pulses which encode data from the source of data;

wherein the medical device further comprises a data detector for extracting the data from the first wireless signal.

2. The medical apparatus as recited in claim 1 wherein the feedback signal generator comprises a detector which senses a characteristic of first wireless signal to produce an indication of the amount of energy.

3. The medical apparatus as recited in claim 2 wherein the detector senses a voltage derived from the first wireless signal.

4. The medical apparatus as recited in claim 1 wherein the feedback signal generator varies the frequency of the second wireless signal in proportion to the amount of energy extracted from the first wireless signal.

5. The medical apparatus as recited in claim 1 wherein the feedback signal generator varies the frequency of the second wireless signal from a predefined frequency in a direction and an amount which indicates deviation of the amount of energy extracted from the first wireless signal from a predefined energy level.

6. The medical apparatus as recited in claim 1 wherein the feedback signal generator comprises:

a detector that senses a voltage derived from the first wireless signal; and the frequency of the second wireless signal is varied from a predefined frequency in a direction and an amount which indicates deviation of the voltage from a predefined voltage level.

7. The medical apparatus as recited in claim 1 wherein the first and second wireless signals are radio frequency signals.

8. The medical apparatus as recited in claim 1 wherein the medical device further comprises a circuit for stimulating tissue of the patient.

9. The medical apparatus as recited in claim 1 wherein the extracorporeal power supply further comprises a pulse width modulator that varies a duty cycle of the first wireless signal in response to the feedback controller to control an amount of energy transmitted to the medical device.

10. The medical apparatus as recited in claim 9 wherein the extracorporeal power supply further comprises an amplitude modulator that varies an amplitude of the first wireless signal in response to the feedback controller to control an amount of energy transmitted to the medical device.

11. The medical apparatus as recited in claim 1 wherein the feedback controller comprises a proportional-integral controller that receives a signal indicating how much the amount of energy extracted from the first wireless signal deviates from a reference value and produces an output signal that controls transmission of the first wireless signal.

12. The medical apparatus as recited in claim 1 wherein the medical device further acquires data and comprises a data modulator that modulates the second wireless signal with the data; and further comprising a data receiver that extracts the data from the second wireless signal.

13. The medical apparatus as recited in claim 12 further comprising a device coupled data receiver to generate an alarm signal in response to the data extracted from the second wireless signal.

14. A medical apparatus comprising an extracorporeal power supply forming a wireless closed loop system with intravascular medical device adapted for implantation into a patient, wherein:
the intravascular medical device comprises a first receiver for a first wireless signal, a power circuit that extracts energy from the first wireless signal to power the intravascular device, and a feedback signal generator that transmits a second wireless signal that indicates an amount of energy extracted from the first wireless signal; and
the extracorporeal power supply comprises a source of electrical power, a power transmitter that emits the first wireless signal, a second receiver for the second wireless signal, a feedback controller connected to the second receiver and the power transmitter and including a proportional-integral controller that receives an indication of how much the amount of energy extracted from the first wireless signal deviates from a reference energy level and produces an output signal that controls transmission of the first wireless signal.

15. The medical apparatus as recited in claim 14 wherein the feedback signal generator varies a frequency of the second wireless signal in proportion to the amount of energy extracted from the first wireless signal.

16. The medical apparatus as recited in claim 15 wherein the feedback signal generator varies the frequency of the second wireless signal from a predefined frequency in a direction and an amount which indicates deviation of the amount of extracted energy from a predefined energy level.

17. The medical apparatus as recited in claim 14 wherein the first and second wireless signals are radio frequency signals.

18. The medical apparatus as recited in claim 14 wherein the extracorporeal power supply further comprises a pulse width modulator that varies a duty cycle of the first wireless signal in response to the feedback controller.

19. The medical apparatus as recited in claim 14 wherein:
the extracorporeal power supply further comprises a source of operational data for the medical device, and a data modulator coupled to the source and the power transmitter to modulate the first wireless signal in response to the operational data; and
the medical device further comprises a data detector for extracting the operational data from the first wireless signal.

20. The medical apparatus as recited in claim 19 wherein the first wireless signal comprises power pulses, each of which having a series of sub-pulses that encode the operational data.

21. The medical apparatus as recited in claim 14:
wherein the medical device further acquires data and comprises a data modulator which modulates the second wireless signal with the data; and
further comprising a data receiver which extracts the data from the second wireless signal.

22. The medical apparatus as recited in claim 21 further comprising a device coupled data receiver to generate an alarm signal in response to the data extracted from the second wireless signal.

23. A method for controlling electrical energy delivered from an extracorporeal power supply to a medical device implanted in a patient, the method comprising:
transmitting, from the extracorporeal power supply, a first wireless signal having an energy level;
receiving the first wireless signal at the medical device implanted in a patient;
the medical device extracting electrical energy from the first wireless signal;
transmitting from the medical device a second wireless signal having a frequency that varies to indicate an amount of electrical energy extracted from the first wireless signal;
receiving the second wireless signal at the extracorporeal power supply, wherein the receiving comprises producing a deviation signal that represents a difference between a predefined frequency and the frequency of the second wireless signal; and
in response to the frequency of the second wireless signal, manipulating transmission of the first wireless signal to control the energy level, wherein the manipulating is in response to a value equal to an arithmetic difference between a setpoint frequency and the product of a time independent constant gain factor and the time integral of the deviation signal.

24. The method as recited in claim 23 wherein extracting electrical energy from the first wireless signal comprises producing an electrical voltage, and wherein the second wireless signal indicates a magnitude of the electrical voltage.

25. The method as recited in claim 23 wherein manipulating transmission of the first wireless signal comprises varying a duty cycle in response to the second wireless signal.

26. The method as recited in claim 23 further comprising:
providing data specifying an operational parameter for the medical device; and
modulating the first wireless signal with the data.

27. The method as recited in claim 26 wherein the first wireless signal comprises power pulses, and modulating the first wireless signal comprises forming each power pulse with a series of sub-pulses that encode the data.

28. The method as recited in claim 23 further comprising:
the medical device acquiring data and modulating the second wireless signal with the data; and
further comprising a data receiver for extracting the data from the second wireless signal.

29. The method as recited in claim 28 further comprising generating an alarm signal in response to the data extracted from the second wireless signal.

* * * * *